April 9, 1946. W. E. LAMMERTS Plant Pat. 677
ROSE PLANT
Filed Jan. 23, 1945
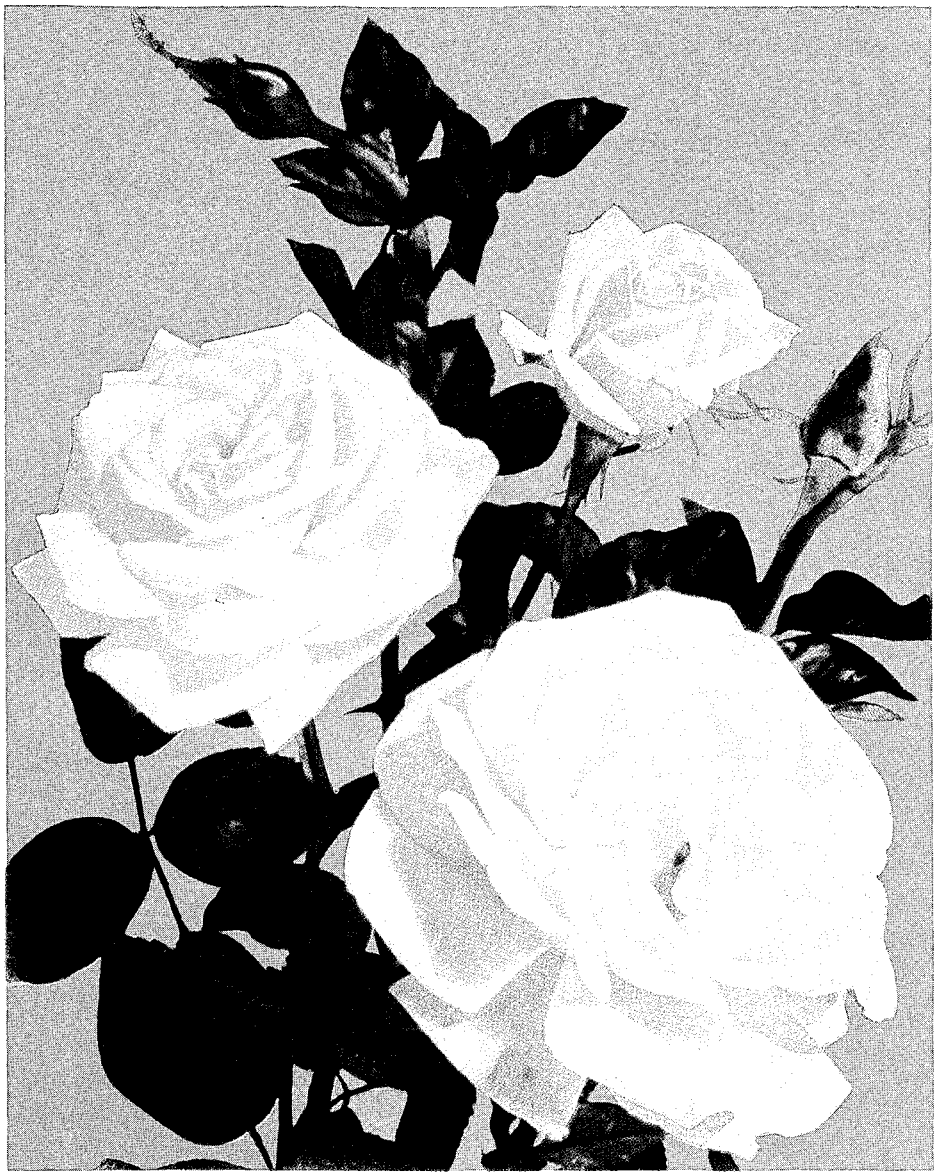
Inventor
W. E. Lammerts
By Robbins & Robbins
His Attorneys

UNITED STATES PATENT OFFICE

677

ROSE PLANT

Walter E. Lammerts, West Los Angeles, Calif., assignor to Armstrong Nurseries, Inc., Ontario, Calif., a corporation of California Application January 23, 1945, Serial No. 574,106

1 Claim. (Cl. 47—61)

The present invention relates to a novel and distinct variety of hybrid tea rose, originating by the crossing of the well known rose "Golden Rapture" (American name for Geheimrat Duisberg) with an unnamed seedling, and resulting in a yellow rose having a combination of desirable characters not present in yellow roses now in commerce.

Referring to the novel characteristics, it may be noted that the new variety plant is a very vigorous, bushy one, abundantly clothed with medium to large, flat leaves of a tough, glossy character. This foliage is very handsome in appearance and is almost entirely resistant to mildew.

The flower of the new variety is a large semi-double to double flower of average intensity of yellow color, but is composed of petals of better than the average substance for yellow roses.

Furthermore, the buds of the new variety are ovoid in shape with reflex petal tips, high centered in respect to a newly opened flower, and loosely flat in the full blown flower.

All of these characteristics are quite important in relation to a rose of yellow color, because up to the present time, so far as I am aware, such combination of desirable features has not been found to exist.

Asexual reproduction of this new variety shows the foregoing characteristics come true to form and are established.

The drawing shows specimens of this variety in various stages of development.

The following is a detailed description of this new variety, the color terminology being in accord with the Robert F. Wilson Horticultural Colour Chart, except where otherwise designated as taken from Ridgway's Color Standard:

Type: Bush; seedling; for cut flowers and garden decoration.
Class: Hybrid tea.
Breeding:
*Seed parent.*—"Golden Rapture."
*Pollen parent.*—Unnamed seedling.
Propagation: Holds its distinguishing characteristics through succeeding propagations by budding, which is the only method tried up to the present.

*flower*

Locality where grown: Ontario, California.
Flowers borne: Singly and three, four, five or several to stem; in irregular cluster; on normal, medium length stems.
Quantity of bloom: Free.
Continuity of bloom: Continuous.
Fragrance: Moderate; tea.
Bud:
*Pedicel.*—Medium length; medium heavy; medium erect; medium rough; numerous gland-tipped cilia. Color—near Lettuce Green, Plate 861.
*Before calyx breaks.*—*Size*—medium. *Form*—short; pointed, without a conspicuous neck; with foliaceous appendages; tomentum; gland-tipped cilia; glandular bloom on the surface of the bud; with slender, much cut, foliaceous parts extending beyond the tip of the bud equal to ¼ to ½ or more of its length.
*As calyx breaks.*—*Color*—base color near Uranium Green, Plate 63/2; blotched and striped with near Mandarin Red, Plate 17/2. *Inner surface*—with fine, wooly tomentum. Margins with usually two sepals with stipitate glands only and three sepals with stipitate glands and wooly tomentum.
*As first petal opens.*—*Size*—medium. *Form*—short to medium; ovoid. *Color*—outside—Mimosa Yellow, Plate 602/1. Curled edge at apex blushed with near Rose Bengal, Plate 25/2; inside—Mimosa Yellow, Plate 602. *Opening*—opens up well.
Bloom:
*Size.*—When fully open, medium size; 3 inches to 4½ inches.
*Petalage.*—Double; 28 to 35 petals arranged regularly except near the center.
*Form.*—High center at first, remaining so until full-bloom when it becomes loosely flat in form.
Petals: Thick; with inside and outside satiny.
*Shape.*—Outside—obovate; scalloped with one to two notches. Intermediate—obovate; usually none, sometimes one notch. Inside—obovate; scalloped with one to two notches.
*Color.*—Colors may be modified by being shaded, washed, or tinted with other colors.

This description of a newly opened flower was made from a rose grown outdoors in the month of September 1944, at Ontario, California:

*Color.*—*Outside petal*—outside surface: basic color, near Empire Yellow, Plate 603/1, becoming darker toward base to near Straw Yellow, Plate 604; lightly tinted with near Rose Bengal, Plate 25/3; inside surface: basic color, near Empire Yellow, Plate 603/1, becoming darker toward base to near Straw Yellow, Plate 604. Lightly tinted with near Rose Bengal, Plate 25/3. *Intermediate petal*—outside surface: near Mimosa Yellow, Plate 602/2; somewhat darker toward base, near Mimosa Yellow, Plate 602; inside surface: near Mimosa Yellow, Plate 602/2; somewhat darker toward base, near Mimosa Yellow, Plate 602. *Inner petal*—outside surface: near Mimosa Yellow, Plate 602/1, becoming darker toward base, near Mimosa Yellow, Plate 602; inside surface: near Mimosa Yellow, Plate 602/1, becoming darker toward base, near Mimosa Yellow, Plate 602.

This description was made from a rose that was open for three days outdoors in the month of September 1944, at Ontario, California:

*Color.*—

*Outside petal*—outside surface: near Primrose Yellow, Plate 601/3, gradually darkening toward base to near Primrose Yellow, Plate 601/2; irregularly blotched toward apex with near Tyrian Rose, Plate 24/2; inside surface: near Primrose Yellow, Plate 601/3, becoming darker toward base to near Primrose Yellow, Plate 601; irregularly blotched toward apex with near Tyrian Rose, Plate 24/2.

*Inside petal*—outside surface: near Primrose Yellow, Plate 601/2, gradually darkening toward base to near Primrose Yellow, Plate 601/1; inside surface: near Primrose Yellow, Plate 601/3, darkening toward base to near Primrose Yellow, Plate 601/1.

*General color effect.*—Newly opened flower—between Empire Yellow, Plate 603/1, and Mimosa Yellow, Plate 601/1. Three days open—near Primrose Yellow, Plate 601/1.

*Behavior.*—Persist slightly; fading brown; color becomes somewhat lighter in shade; affected by hot weather.

*Flower longevity.*—On bush in garden—two to three days in September. Cut roses grown outdoors kept at living room temperatures—three to four days in September.

*Reproductive organs*

Stamens: Medium number; arranged irregularly about pistils, mixed with petaloids.
Filaments: Medium length; most with anthers.
Anthers: Medium size; all open at once approximately; near Buttercup Yellow, Plate 5/2.
Pollen: Moderate; White.
Pistils: Medium number.
Styles: Uneven; medium length; medium heavy; bunched; color near Rose Madder, Plate 23/1.
Stigma: White.
Ovaries: Enclosed in, some protruding from calyx.
Hips: Does not set hips readily.
Sepals: Permanent; moderately long; spear-shaped; recurved. *Color*—inside—near Agatha Green, Plate 60/2, covered with near white tomentum; outside—near Spinach Green, Plate 0960/1.
Seeds: Few; medium size.

*Plant*

Foliage:

*Leaves.*—Compound of three to five leaflets; normal to abundant; medium to large; moderately heavy; leathery; semi-glossy.

*Leaflets.*—Shape—ovoid; mucronate. Base—obtuse. Margin—irregularly serrate. Serrations reduced at base to stipitate glands.

*Color.*—*Mature*—upper surface—near Spinach Green, Plate 0960/1; under surface—near Biscay Green, Plate XVII (Ridgway). *Young*—upper surface—near and varying from Mars Violet, Plate XXXVIII (Ridgway); under surface—near and varying from Deep Helebore Red, Plate XXXVIII (Ridgway).

*Rachis.*—Light to medium heavy. Upper side—grooved; glandular; under side—moderately prickly.

*Stipules.*—Medium length; medium wide; medium, long points, turning out at an angle of less than 45°, usually recurved toward the stem.

*Disease.*—Resistant to mildew.

Growth:

*Habit.*—Bushy; upright spreading; much branched.

*Growth.*—Moderately vigorous.

*Canes.*—Medium heavy.

*Main stems.*—*Color*—near Biscay Green, Plate XVII (Ridgway), blotched with darker markings of near Light Elm Green, Plate XVII (Ridgway). *Large prickles*—several to many; medium length; straight; with moderately narrow base. Color—near Mimosa Yellow, Plate 602/2. *Small prickles*—none. *Hairs*—none.

*Branches.*—*Color*—near Biscay Green, Plate XVII (Ridgway). Side exposed to sun, near Olive Brown, Plate XL (Ridgway). *Large prickles*—several; medium length; straight; with short narrow base. Color—near Grape Green, Plate XLI (Ridgway). *Small prickles*—few; near Grape Green, Plate XLI (Ridgway). *Hairs*—none.

*New shoots.*—*Color*—near and varying from Dull Indian Purple, Plate XLIV (Ridgway). *Large prickles*—many; medium length; straight; with long, narrow base. Color—near Vinaceous Lilac, Plate XLIV (Ridgway). Points near Grape Green, Plate XLI (Ridgway). *Small prickles*—none. *Hairs*—none.

I claim:

A new and distinct variety of hybrid tea rose, characterized as to novelty by the vigorous and bushy habit of growth of the plant; the abundance of medium to large flat leaves of a tough, glossy character, giving beauty of appearance and resistance to mildew; large, semi-double to double flowers of average intensity of yellow color and composed of petals of better than average substance for yellow roses; ovoid form of bud with reflex petal tips; and high centered newly opening flower and loosely flat full blown flower, substantially as shown and described.

WALTER E. LAMMERTS.